United States Patent [19]

Christensen et al.

[11] 4,432,361
[45] Feb. 21, 1984

[54] PORTABLE CONTINUOUSLY SELF-MONITORING BONE HEALING DEVICE AND METHOD

[75] Inventors: James M. Christensen, San Diego; Allan H. Mizoguchi, Del Mar, both of Calif.

[73] Assignee: Sutter Biomedical Inc., San Diego, Calif.

[21] Appl. No.: 340,520

[22] Filed: Jan. 18, 1982

[51] Int. Cl.³ .............................................. A61N 1/20
[52] U.S. Cl. ................................................ 128/419 F
[58] Field of Search .............. 128/419 F, 419 R, 82.1, 128/798, 784–786

[56] References Cited
U.S. PATENT DOCUMENTS 3,842,841 10/1974 Brighton et al. ................. 128/419 F
4,175,565 11/1979 Chiarenza et al. ............... 128/419 F

FOREIGN PATENT DOCUMENTS

WO81/00964 4/1981 PCT Int'l Appl. ................. 128/798

OTHER PUBLICATIONS

Lavine et al., "Electric . . . Bone Healing" Science, vol. 175, Mar. 1976, pp. 1118–1121.
Zimmer U.S.A., Lit. No. B-2360-1, 1979

*Primary Examiner*—Lee S. Cohen
*Attorney, Agent, or Firm*—Flehr, Hohbach, Test, Albritton & Herbert

[57] ABSTRACT

A completely portable, continuously self-monitoring device for expediting the healing of bone or soft tissue fractures or defects in a patient is disclosed herein along with its method of use. This device includes an electrical power supply, electronic circuitry and an arrangement of electrodes for applying current in a regulated manner through the fracture or defect site in a way which has been found to expedite the healing of bone fractures or bone defects at the site. The device also includes a monitoring arrangement cooperating with its power supply, electronic circuitry and arrangement of electrodes for continuously detecting and visually indicating whether or not the power supply is in proper working order and whether or not current is flowing through the fracture or defect site.

5 Claims, 4 Drawing Figures

PORTABLE CONTINUOUSLY SELF-MONITORING BONE HEALING DEVICE AND METHOD

The present invention relates generally to techniques for expediting the healing of bone fractures or bone defects or soft tissue defects in a patient and more particularly to a completely portable, continuously self-monitoring device for this purpose and its method of use.

The utilization of electric current to aid in expediting the healing of bone fractures or bone defects in a patient is well known in the art and has been the subject of numerous publications. One particular device or system is described in U.S. Pat. No. 3,842,841 (Brighton et al). The system disclosed there utilizes a cathode electrode and an anode electrode in combination with a direct current power supply and suitable circuitry for directing constant DC current into the fracture or defect site. This is accomplished by placing one of the electrodes, specifically the cathode electrode, in the patient at the fracture or defect site while the other electrode, specifically the anode electrode, is placed against the outer skin of the patient but otherwise in close proximity to the cathode electrode. The entire system is sufficiently portable so as to be carried around by the patient.

While the concept of applying a continuous, regulated supply of current into the site of a bone fracture or similar defect in a patient for expediting or otherwise aiding in the healing thereof is a very desirable procedure, applicants have found a major disadvantage to the device described in the Brighton patent. Specifically, although the device includes test leads for monitoring certain aspects of its operation, this requires separate test equipment which is better explained in a publication entitled THE ALTERNATE TREATMENT OF FRACTURE NON-UNION which discusses the ZIMMER (a registered trademark) direct current bone growth stimulator manufactured under a license of the Brighton et al patent. In this publication, the ZIMMER device is described including the same test leads disclosed in the Brighton et al patent. A separate test meter is shown in conjunction with the test leads to periodically check out the device. In accordance with the post operative treatment and followup procedure described in this publication, a patient using the ZIMMER device is required to return to his doctor or the clinic at successive intervals, specifically at intervals of four and eights weeks and thereafter at twelve weeks, in order to have the device checked out from an operational standpoint, presumably utilizing the test meter. In the meantime, the patient has no idea whether the device is functioning properly or at all. If it is not, precious time will have been lost between visits to the doctor or clinic and, at best, even if the device is in proper working order, the patient not knowing this can be subjected to a certain amount of anxiety.

In view of the foregoing, it is a primary object of the present invention to provide a portable device for expediting the healing of bone or soft tissue fractures or defects in a patient and its method of use and particularly a device which is continuously self-monitoring during operation thereof in a way which always apprises the patient carrying the device of its operative status.

Another object of the present invention is to provide the self-monitoring feature just recited in an uncomplicated and reliable manner and specifically a manner which readily visually indicates to the patient the operative status of the device carried by him or her.

As will be described in more detail hereinafter, the device for expediting the healing of bone or soft tissue fractures or defects disclosed herein is completely portable and, as indicated above, continuously self-monitoring. This device utilizes means including an electrical power supply and at least one but preferably a number of active or cathode electrodes (hereinafter "cathodes") and a single ground or anode electrode (hereinafter "anode") for applying a regulated flow of current between the electrodes and into the fracture or defect site in the patient. At the same time, the device is provided with monitoring means cooperating with the last-mentioned means for continuously detecting and indicating, preferably visually, whether or not the power supply is in operational and whether or not the minimum required amount of current is flowing between each cathode electrode and the anode electrode. In a preferred embodiment, the visual indicating means includes separate visually observable indicia relating to the status of the power supply and each circuit formed by the various cathodes and the anode.

The device briefly discussed above and its method of use will be described in more detail hereinafter in conjunction with the drawings wherein.

Figure 1:
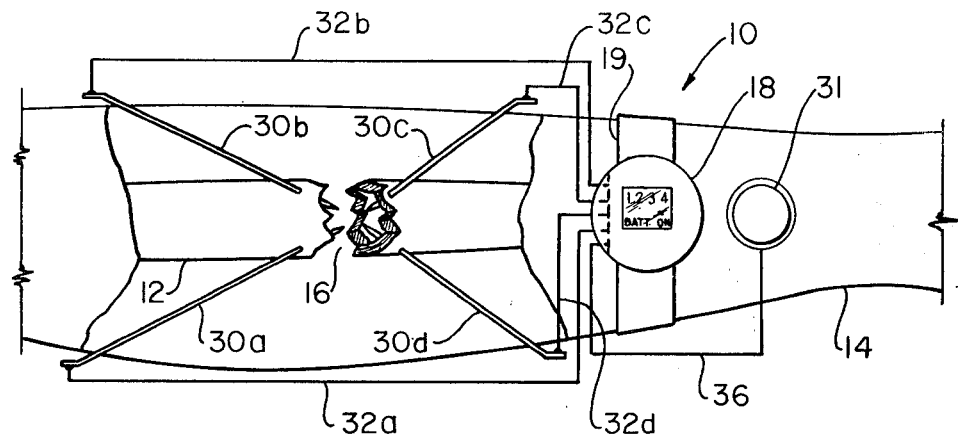
FIG. 1 is a schematic illustration of the device shown in an operating position for expediting or otherwise aiding in the healing of a bone fracture in a patient's leg.

Turning now to the drawings, wherein like components are designated by like reference numerals throughout the four figures, attention is first directed to FIG. 1. A completely portable, continuously self-monitoring device for expediting the healing of bone fractures, bone defects or the like in a patient is illustrated and generally designated by the reference numeral 10. As stated above, device 10 is shown in an operating position for expediting or otherwise aiding in the healing of a fractured bone 12 in the leg 14 of a particular patient. To this end, device 10 is designed to cause direct current to flow through the site 16 of the fracture in a regulated fashion, as will be discussed in more detail hereinafter. Since the orthopedic advantages achieved as a result of this procedure are well recognized in the art, they will not be described herein, except as previously set forth. This is also true with respect to the amount of current which is utilized, the particular way it is applied to the fracture site and other details relating directly to the healing procedure. The prior art including the previously discussed Brighton et al patent and the ZIMMER publication as well as other prior publications discuss necessary details associated with the healing procedure itself and the way in which a device such as device 10 must operate to carry out this procedure.

Figure 2:
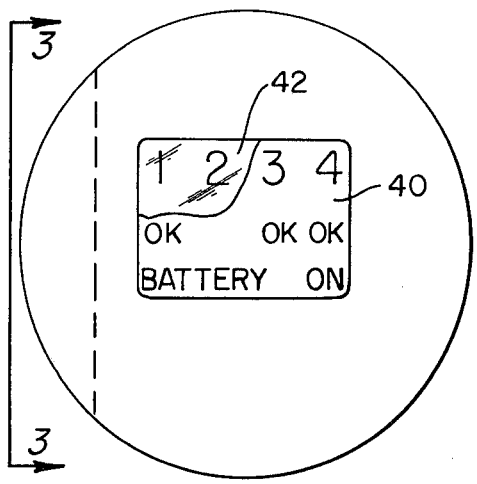
FIG. 2 is a plan view of a part of the device illustrated in FIG. 1, specifically its casing or housing which contains certain electronics and a viewing window for indicating the status of certain operating aspects of the device.
Figure 3:
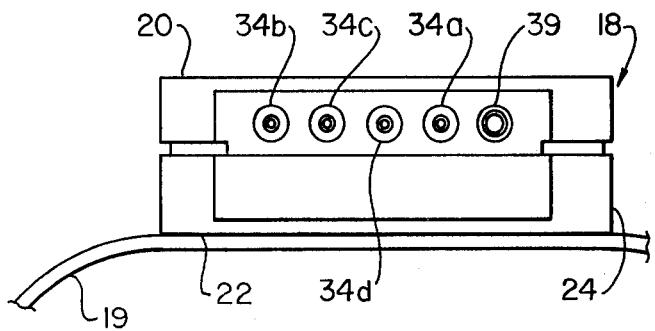
FIG. 3 is a side view of the housing illustrated in FIG. 2, taken generally along line 3—3 in FIG. 2.

With reference to FIG. 1 in conjunction with FIGS. 2 and 3, overall device 10 is shown including a casing or housing 18 which is sufficiently small and which, along with all of the components contained therein, is sufficiently light in weight to be easily carried by the patient, for example around his leg as shown in FIG. 1. To this end, any suitable means such as a strap 19 is utilized to hold the casing in place. In the particular embodiment shown in FIGS. 1–3, the casing is somewhat cylindrical in shape so as to define a top side 20, a bottom side 22 and a circumferential side wall 24. Strap 19 is bonded or otherwise fixedly attacted to bottom side 22 and is designed to support the casing against the patient's leg 14 so as to readily expose top side 20 to view, as seen in FIG. 1.

In addition to casing 18 and strap 19 (or other suitable means), overall device 10 includes a portable electric power supply 38 (see FIG. 4), for example a battery which may or may not be of a rechargeable type, contained within casing 18, a plurality of cathode electrodes 30, a single anode electrode 31 and overall electronic circuitry 33 (again, see FIG. 4) also contained within casing 18 and provided for the reasons to be discussed below. In the particular embodiment illustrated, device 10 is shown including four cathodes 30 which are individually indicated as 30A, 30B, 30C and 30D. Each of these electrodes is in the form of a relatively rigid pin which is electrically conductive. Pointed end sections of these pins may be located in predetermined positions within the fracture site 16, as shown. The exposed ends of these pins are respectfully connected electrically to the ends of electrical lead wires 32A, B, C and D. The other ends of these lead wires include suitable means for electrically plugging into cooperating terminals in the side wall of casing 18 for electrically connecting the cathode electrodes into the circuitry contained within casing, as will be discussed with respect to FIG. 4. The four terminals are illustrated in FIG. 3 at 34A, B, C and D.

The anode electrode 31 is placed at a predetermined position against the outer skin of the patient in close proximity to fracture site 16. Anode 31 is electrically connected into the circuitry contained by casing 18 utilizing a fifth lead wire 36 which is connected at one end to the anode and which includes suitable means for plugging into a cooperating terminal 38 in the side wall of the casing, as shown in FIG. 3. Anode 31 may be of any suitable and readily providable type so long as it provides for a reliable electric connection between the patient's skin and the circuitry within casing 18.

As stated above, the electrical circuitry 33 contained within casing 18 will be described in more detail hereinafter in conjunction with FIG. 4. For the moment, it should suffice to say that this circuitry cooperates with the device's power supply, e.g. battery 38, and the arrangement of electrodes so as to cause a regulated supply of current to flow from the power supply through and between each of the cathodes 30 and anode 31, thereby causing the current to flow into and through fracture site 16 shown in FIG. 1. In most if not all cases, device 10 is provided to operate in this manner continuously for relatively long periods, for example on the order of weeks or months.

In order to reassure the patient that device 10 is in proper working order or to let him know immediately when it is not, the device includes its own monitoring arrangement which cooperates with the power supply, the electrodes 30 and 31 and their associated circuitry during operation of the device for continuously detecting and visually indicating whether or not the power supply is in operating order and whether or not the minimum desired amount of current is flowing between each of the cathodes 30 and the anode 31. This monitoring arrangement is in part comprised of electronic circuitry illustrated in FIG. 4 and also includes a visual readout display (a liquid crystal display) 40 contained within casing 18 and disposed directly under and in alignment with a viewing window 42 (see FIG. 2) in top side 20 of the casing. This visual display includes fixed indicia, specifically the words BATTERY ON and the numerals 1, 2, 3 and 4; assuming the battery is operative, otherwise no indicia at all will appear at the viewing window, as will be seen. The visual display may include nothing else or it may include the designation OK next to each of the fixed numerals. So long as a minimum selected amount of electric current passes between each of the four cathodes 30 and the anode 31, the designation OK is provided adjacent the corresponding number. As the display is shown in FIG. 2, the battery is on and so are the current paths 1, 3 and 4 between corresponding cathodes 30 and the anode 31. However, the circuit path 2 between the fourth cathode 30 and the anode is not functioning and therefore readily and immediately apparent to the patient. The patient does not have to worry between relatively extended office visits to the doctor or clinic whether or not the device is operating properly.

Figure 4:
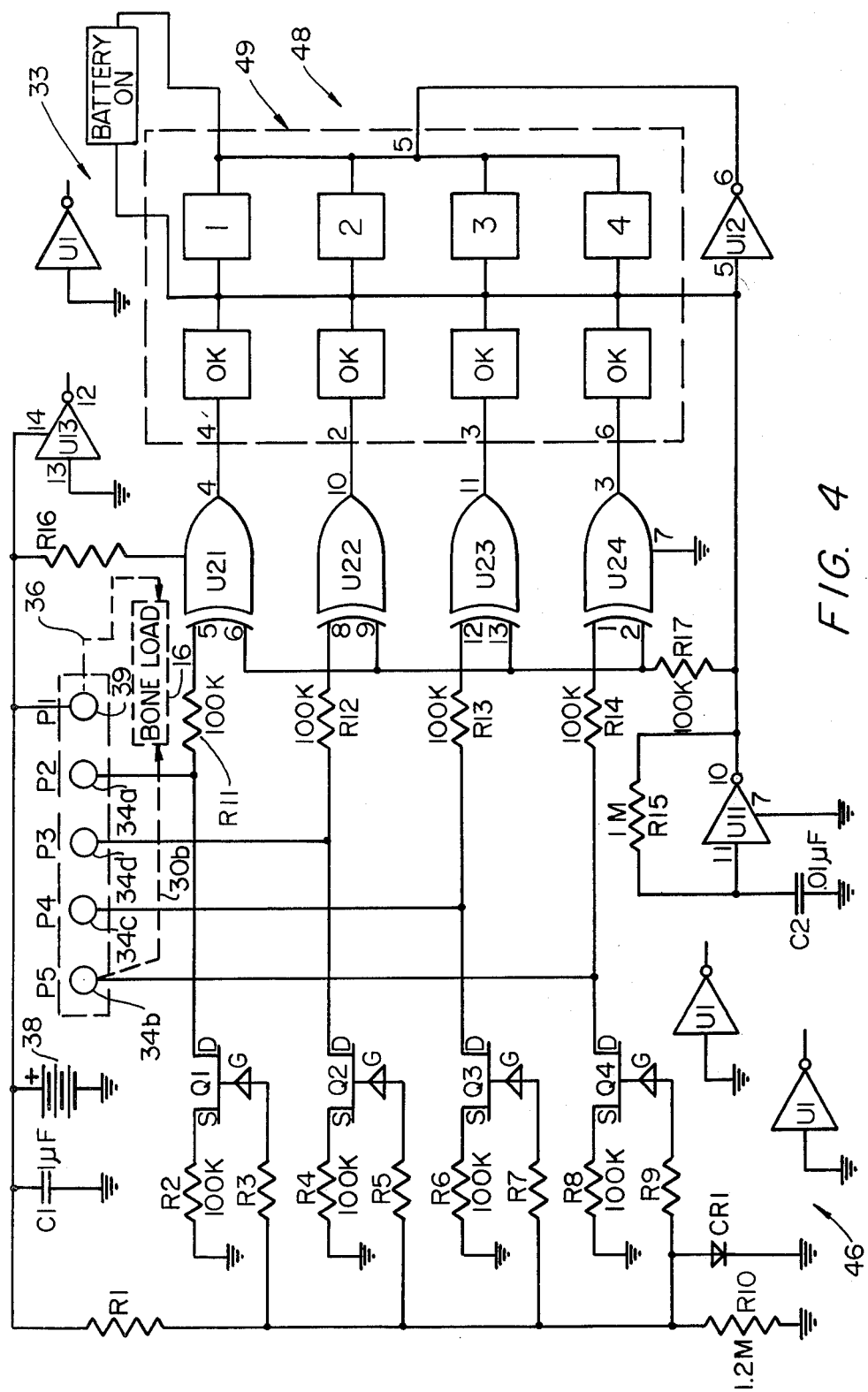
FIG. 4 is a schematic illustration of the circuitry utilized by the device illustrated in FIG. 1 for its operation.

Turning now to FIG. 4, attention is directed to overall circuitry 33 contained within casing 18. This circuitry includes the previously recited power supply, that is, battery 38, as well as the terminals 34A–34D and 39. These latter terminals are also indicated as P1–P5. Terminal P1 is adapted to electrically receive anode 31 and the terminals P2–P5 are provided for electrically receiving to the cathodes 30, as discussed above. Circuitry 33 may be divided into two circuit arrangements, a power circuit 46 and a monitoring circuit 48. The power circuit serves to deliver a regulated amount of current between each cathode and the anode through the fracture site 16 when the electrodes are positioned in the manner illustrated in FIG. 1. The monitoring circuit 48 serves to detect and visually indicate whether or not the appropriate amount of current is being provided between each cathode and the anode and whether or not the battery is functioning.

Referring first to the power circuit 46, as shown in FIG. 4, this circuit includes battery 38, the terminals P1–P5 and four constant current devices, specifically field effect transistors (FETS) Q1, Q2, Q3 and Q4, respectfully connected at their drain electrodes to the terminals P2–P5. The source electrodes of the FETS are grounded through current regulating resistors R2, R4, R6 and R8. Finally, the gate electrodes of the FETS are connected through respective current limiting resistors R3, R5, R7 and R9 to a temperature compensating circuit consisting of resistors R1 and R10 and diode CR1. The capacitor C1 serves as a decoupling capacitor.

Assuming that the cathodes 30 and that the anode 31 are placed in their respective operating positions such as the position illustrated in FIG. 1 and assuming battery 38 is in proper working order, circuit 46 operates in the following manner to provide a fixed, regulated level of DC current between each cathode and the anode through the fracture site (e.g. through the bone which serves as a load). In actual practice, current flows from the cathode through the fracture site and into each anode. Turning for example to the cathode 30B, it can be seen from the arrows in FIG. 4 that current is delivered from the positive side of the battery through the anode electrode and the fracture site (e.g. the bone) and thereafter into the cathode 30B. From this point, e.g. P5, the current passes across field effect transistor Q4 from its drain electrode to its supply electrode and finally to ground through current regulating resistor R8. The exact amount of current which is provided depends upon resistor R8 and FET Q4. In an actual working embodiment, resistor R8 is selected to provide 20 microamps ±1 microamp. The other three anode/cathode circuits including field effect transistors Q1, Q2 and Q3 operate in the same manner and their respective current regulating resistors R2, R4 and R6 are designed to provide the same amount of current. In other words, approximately 20 microamps of current flows between the anode and each cathode in an actual working embodiment.

Having described power circuit 46, attention is now directed to monitoring circuit 48 which, as stated previously, is provided for detecting and visually indicating whether or not the battery is on and whether or not there is at least the regulated amount of current passing between the anode and each cathode, e.g. the selected 20 microamps ±1 microamp. In order to provide this end result, monitoring circuitry 48 includes a hex inverter which is a solid state device containing six inverters, only three of which are used. These inverters are designated as U11, U12 and U13. Circuit 48 also includes four EXCLUSIVE OR gates U21, U22, U23 and U24 and a liquid crystal display (LCD) assembly 49. This LCD assembly includes the indicia 1, 2, 3, 4, the designation OK adjacent to each and the phrase BATTERY ON. Finally, circuitry 48 includes current limiting resistors R11, R12, R13, R14, R16 and R17 as well as a square wave oscillator consisting of one of the inverters, specifically inverter U11, resistor R15 and capacitor C2.

Assuming that overall device 10 is operating properly to provide the desired current between each cathode and the anode, circuit 48 operates in the following manner. First, battery 38 provides power to the square wave oscillator through terminal 14 of the hex inverter. The square wave oscillator responds to this power by producing a square wave of fixed amplitude and frequency at its output point 10. This square wave signal is applied to the input terminals 6, 9, 13 and 2 of the EXCLUSIVE OR gates and at the same time to the input terminal 1 of the LCD assembly. The second inverter U12 serves to receive the square wave signal and inverts it for application to the input 5 of the LCD assembly. Since the signal is applied to both sides of the indicia 1, 2, 3, 4 and BATTERY ON (at LCD inputs 1 and 5), each of these remains on so long as the battery is in proper operating order.

The indicia OK associated with each of the numerals 1–4 is turned on when its associated LCD input 4, 2, 3 or 6, respectively, receives the square wave signal 50. For example, in the case of the OK associated with the reference numeral 1, the LCD input 4 is connected to the output of EXCLUSIVE OR gate U21. As stated previously, its input 6 is connected to the square wave oscillator to receive the square wave signal. At the same time, its input 5 is connected through current limiting resistor 11 to the drain side of FET Q1. So long as the current passing through Q1 is equal to the regulated level, e.g. 20 microamps ±1 microamp, gate U21 will sense this and function to pass the square wave signal of the proper phase, thereby turning on its associated indicia OK for visually indicating that the desired amount of current is passing between the cathode 30A and anode 31. However, should the current level drop below the regulated level, that is, below the 20 microamps ±1 microamp in the actual working embodiment, the gate U21 will reverse the square wave signal phase to its output which, in turn, will cause its associated OK indicia to turn off, thereby visually indicating that the current level between cathode 30A and anode 31 is below the desired level. Because of the various current limiting features of the overall circuitry, there is no need to provide detecting and indicating means for the situation where the current is above 20 microamps ±1 microamp between the anode and cathode.

The monitoring aspects of circuitry 48 with respect to the other cathodes and the anode are the same as described above and hence will not be described herein. It suffices to say that each indicia OK will remain on so long as the regulated amount of current passes between the anode and each cathode. At the same time, so long as the battery is in proper operating order, the indicia BATTERY ON will be visible. In the event that the battery stops functioning, all of the indicia will go out including the words BATTERY ON.

As stated previously, in an actual working embodiment, overall circuitry 44 provides 20 microamps ±1 microamp of direct current between the anode and each cathode. In FIG. 4, the circuitry shown is based on this specific embodiment and therefore provides corresponding values for its various components. In the case of 20 microamps ±1 microamp, each of the resistors R2, R4, R6 and R8 are selected to be 15–16K ohms. The hex inverter (inverters U11, U12 and U13) is a National Semiconductor hex inverter, part No. MM74C14N and the EXCLUSIVE OR gates are National Semiconductor devices part No. MC14070BCP. It is of course to be understood that this specific working embodiment is being provided for exemplary purposes only and is not intended to limit the present invention.

While the device 10 has been described in connection with a bone fracture, it is to be understood that the device can be used to heal other types of bone defects and soft tissue defects such as torn ligaments.

What is claimed is:

1. A completely portable, continuously self-monitoring device for expediting the healing of bone or soft tissue fractures or defects in a patient, said device comprising: an electrical power supply, a plurality of first electrodes, a second electrode and circuit means cooperating with said power supply for applying a regulated flow of current between each of said first electrodes and said second electrode through the fracture or defect site in the patient by the appropriate placement of said electrodes relative to said site; and monitoring means cooperating with said power supply, all of said electrodes and said circuit means during operation of the device for continuously detecting and visually indicating whether or not said power supply is in operating order and whether or not a minimum predetermined amount of current is flowing between each of said first electrodes and said second electrode, said monitoring means including means for visually indicating whether or not said power supply is in operating order and whether or not current is flowing between each of said first electrodes and said second electrode, said visual indicating means including fixed indicia representing that the power supply is on and representing the circuit paths between corresponding first electrodes and the second electrode so long as the power supply is in operating order and, if said power supply is in operating order, changeable indicia adjacent the fixed indicia for indicating whether or not at least said predetermined amount of current is flowing between each of said first electrodes and said second electrode.

2. A device according to claim 1 including housing means for containing said power supply, said circuit means and said monitoring means, said housing means and the components contained thereby being sufficiently small and lightweight to be easily carried by said patient.

3. A device according to claim 2 wherein said housing means includes a viewing window and wherein said visual indicating means includes a visual display readily observable by the patient through said viewing window.

4. A device according to claim 1 including means for securing said power supply, circuit means and monitoring means to said patient whereby during operation of the device the latter can be carried around by the patient.

5. A completely portable, continuously self-monitoring device for expediting the healing of bone or soft tissue fractures or defects in a patient, said device comprising:

an electrical power supply;

a plurality of first electrodes adapted for placement at predetermined positions within said patient at the fracture or defect site;

a second electrode adapted for placement at a predetermined position against the outer skin of the patient in close proximity to the fracture or defect site;

electronic circuitry means interconnecting said electrodes with said power supply so as to cause a regulated supply of current to flow between each of said first electrodes and said second electrode through said fracture or defect site when said electrodes are placed in said predetermined positions;

monitoring means cooperating with said power supply, electronic circuitry means and electrodes during operation of the device for continuously detecting and visually indicating whether or not said power supply is in operating order and whether or not a minimum predetermined amount of current is flowing between each of said first electrodes and said second electrodes, said monitoring means including indicia for visually indicating whether or not said power supply is in proper operating order and whether or not said minimum predetermined amount of current is flowing between each of said first electrodes and said second electrode, said indicia including the words BATTERY ON and the numerals 1, 2, 3 and 4 corresponding to circuit paths between four first electrodes and said second electrode so long as the power supply is in operating order and the indication OK by each numeral so long as said medium predetermined amount of current flows through the path corresponding to that number; and housing means for containing said power supply, said electronic circuitry means and said monitoring means, said housing means and the components contained thereby being sufficiently small and lightweight to be easily carried by said patient and said housing means including a viewing window through which the patient can observe the indicia forming part of said monitoring means.

* * * * *